United States Patent
Ding et al.

(10) Patent No.: US 7,546,162 B2
(45) Date of Patent: *Jun. 9, 2009

(54) AUTOMATIC SELECTION OF STIMULATION CHAMBER FOR VENTRICULAR RESYNCHRONIZATION THERAPY

(75) Inventors: Jiang Ding, Maplewood, MN (US); Julio C. Spinelli, Shoreview, MN (US); Yinghong Yu, Maplewood, MN (US); Andrew P. Kramer, Stillwater, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 404 days.

This patent is subject to a terminal disclaimer.

(21) Appl. No.: 11/276,007

(22) Filed: Feb. 9, 2006

(65) Prior Publication Data

US 2006/0116727 A1    Jun. 1, 2006

Related U.S. Application Data

(63) Continuation of application No. 10/655,569, filed on Sep. 4, 2003, now Pat. No. 6,999,815, which is a continuation of application No. 09/738,407, filed on Dec. 15, 2000, now Pat. No. 6,622,040.

(51) Int. Cl.
    *A61N 1/365* (2006.01)
(52) U.S. Cl. .......................................... 607/30; 607/9
(58) Field of Classification Search .................. 607/9, 607/30
    See application file for complete search history.

(56) References Cited

U.S. PATENT DOCUMENTS

| | | | |
|---|---|---|---|
| 4,928,688 A | 5/1990 | Mower | |
| 5,174,289 A | 12/1992 | Cohen | |
| 5,267,560 A | 12/1993 | Cohen | |
| 5,487,752 A | 1/1996 | Salo et al. | |
| 5,507,782 A | 4/1996 | Kieval et al. | |
| 5,540,727 A | 7/1996 | Tockman et al. | |
| 5,697,959 A * | 12/1997 | Poore | 607/32 |
| 5,713,937 A * | 2/1998 | Nappholz et al. | 607/30 |
| 5,792,203 A | 8/1998 | Schroeppel | |
| 5,817,137 A * | 10/1998 | Kaemmerer | 607/59 |
| 5,891,178 A | 4/1999 | Mann et al. | |
| 6,129,744 A * | 10/2000 | Boute | 607/25 |
| 6,249,705 B1 | 6/2001 | Snell | |
| 6,272,377 B1 | 8/2001 | Sweeney et al. | |

(Continued)

*Primary Examiner*—George R Evanisko
*Assistant Examiner*—Amanda Patton
(74) *Attorney, Agent, or Firm*—Schwegman, Lundberg & Woessner, P.A.

(57) ABSTRACT

A method and apparatus for selection of one or more ventricular chambers to stimulate for ventricular resynchronization therapy. Intrinsic intracardia electrograms that include QRS complexes, are recorded from a left and right ventricle. A timing relationship between the intrinsic intracardia electrograms recorded from the left and right ventricle is then determined. In one embodiment, the timing relationship is determined using a delay between a left ventricular and a right ventricular sensed intrinsic ventricular depolarizations and a duration interval of one or more QRS complexes. In one embodiment, the duration of QRS complexes is determined from either intracardiac electrograms or from surface ECG recordings. One or more ventricular chambers in which to provide pacing pulses are then selected based on the timing relationship between intrinsic intracardia electrograms recorded from the right and left ventricle, and the duration of one or more QRS complexes.

20 Claims, 6 Drawing Sheets

U.S. PATENT DOCUMENTS

| | | | |
|---|---|---|---|
| 6,370,427 B1 * | 4/2002 | Alt et al. ................ 607/4 |
| 6,622,040 B2 | 9/2003 | Ding et al. |
| 6,999,815 B2 | 2/2006 | Ding et al. |
| 7,070,562 B2 | 7/2006 | Bardy |
| 7,136,707 B2 | 11/2006 | Hall et al. |
| 7,181,285 B2 | 2/2007 | Lindh et al. |
| 2004/0133246 A1 | 7/2004 | Ding et al. |
| 2007/0250125 A1 | 10/2007 | Lindh et al. |

* cited by examiner

AUTOMATIC SELECTION OF STIMULATION CHAMBER FOR VENTRICULAR RESYNCHRONIZATION THERAPY

CROSS-REFERENCE TO RELATED APPLICATIONS

This application is a continuation of U.S. patent application Ser. No. 10/655,569, filed on Sep. 4, 2003, now issued as U.S. Pat. No. 6,999,815, which is continuation of U.S. patent application Ser. No. 09/738,407, filed on Dec. 15, 2000, now issued as U.S. Pat. No. 6,622,040, the specifications of which are incorporated herein by reference.

TECHNICAL FIELD

The present invention relates to medical devices and in particular to a medical device for automatically selecting stimulation chamber, or chambers, based on sensed cardiac signals.

BACKGROUND

When functioning properly, the human heart maintains its own intrinsic rhythm, and is capable of pumping adequate blood throughout the body's circulatory system. However, some people have irregular cardiac rhythms, referred to as cardiac arrhythmias. Such arrhythmias result in diminished blood circulation. One mode of treating cardiac arrhythmias uses drug therapy. Drugs are often effective at restoring normal heart rhythms. However, drug therapy is not always effective for treating arrhythmias of certain patients. For such patients, an alternative mode of treatment is needed. One such alternative mode of treatment includes the use of a cardiac rhythm management system. Such systems are often implanted in the patient and deliver therapy to the heart.

Cardiac rhythm management systems include, among other things, pacemakers, also referred to as pacers. Pacers deliver timed sequences of low energy electrical stimuli, called pace pulses, to the heart, such as via an intravascular leadwire or catheter (referred to as a "lead") having one or more electrodes disposed in or about the heart. Heart contractions are initiated in response to such pace pulses (this is referred to as "capturing" the heart). By properly timing the delivery of pace pulses, the heart can be induced to contract in proper rhythm, greatly improving its efficiency as a pump. Pacers are often used to treat patients with bradyarrhythmias, that is, hearts that beat too slowly, or irregularly.

Cardiac rhythm management systems also include cardioverters or defibrillators that are capable of delivering higher energy electrical stimuli to the heart. Defibrillators are often used to treat patients with tachyarrhythmias, that is, hearts that beat too quickly. Such too-fast heart rhythms also cause diminished blood circulation because the heart isn't allowed sufficient time to fill with blood before contracting to expel the blood. Such pumping by the heart is inefficient. A defibrillator is capable of delivering a high energy electrical stimulus that is sometimes referred to as a defibrillation countershock. The countershock interrupts the tachyarrhythmia, allowing the heart to reestablish a normal rhythm for the efficient pumping of blood. In addition to pacers, cardiac rhythm management systems also include, among other things, pacer/defibrillators that combine the functions of pacers and defibrillators, drug delivery devices, and any other implantable or external systems or devices for diagnosing or treating cardiac arrhythmias.

One problem faced by cardiac rhythm management systems is the treatment of heart failure (also referred to as "HF"). Heart failure, which can result from long-term hypertension, is a condition in which the muscle in the walls of at least one of the right and left sides of the heart deteriorates. By way of example, suppose the muscle in the walls of the left side of the heart deteriorates. As a result, the left atrium and left ventricle become enlarged, and the heart muscle displays less contractility. This decreases cardiac output of blood through the circulatory system which, in turn, may result in an increased heart rate and less resting time between heartbeats. The heart consumes more energy and oxygen, and its condition typically worsens over a period of time.

A deterioration of the heart's conduction system often accompanies heart failure. Normally, intrinsic signals of the heart's conduction system originate in the sinoatrial (SA) node in the upper right atrium. These signals travel through and depolarize the atrial heart tissue to trigger the contraction of the right and left atria. The intrinsic atrial heart signals are received by the atrioventricular (AV) node which, in turn, triggers a subsequent ventricular intrinsic heart signal that travels through the specialized conduction system (Purkinje Fibers) and depolarizes the ventricular heart tissue such that resulting contractions of the right and left ventricles are triggered substantially simultaneously.

In the above example, when the left side of the heart has become enlarged due to heart failure and the conduction system in the left ventricle is blocked, the ventricular intrinsic heart signals may travel through and depolarize the left side of the heart more slowly than in the right side of the heart. This condition is referred to as left bundle branch block (LBBB). As a result, the left and right ventricles do not contract simultaneously, but rather, the left ventricle contracts after the right ventricle. This reduces the pumping efficiency of the heart. Moreover, in the case of LBBB, for example, different regions within the left ventricle may not contract together in a coordinated fashion.

Heart failure can be treated by biventricular (or left-ventricular) coordination therapy that provides pacing pulses to both right and left ventricles. See, e.g., Mower U.S. Pat. No. 4,928,688. Heart failure may also result in an overly long atrioventricular (AV) delay between atrial and ventricular contractions, again reducing the pumping efficiency of the heart. Providing heart failure patients with improved pacing and coordination therapies for improving AV-delay, coordinating ventricular contractions, or otherwise increasing heart pumping efficiency continues to be an area in which improved techniques and therapy protocols are needed.

SUMMARY

The present subject matter provides for improved pacing and coordination therapies for heart failure patients. The present subject matter includes a method and apparatus for recording intrinsic electrograms, including QRS complexes, of left and right ventricles. A timing relationship is then determined between the intrinsic electrograms of the left and the right ventricles. A selection of one or more ventricular chambers in which to provide pacing pulses is then made based on the timing relationship between intrinsic electrograms of the left and the right ventricles.

In one embodiment, determining the timing relationship includes calculating a delay between a left ventricular and a right ventricular sensed intrinsic ventricular depolafizations and measuring a duration interval of one or more QRS complexes. In one embodiment, intrinsic intracardia electrograms are sensed of the left and right ventricles. The delay is determined by detecting peaks of the sensed intrinsic ventricular depolarizations and calculating the delay between the detected peaks of the intrinsic ventricular depolarizations sensed from the left ventricular and the right ventricles. Additionally, the duration of the QRS complexes are determined from either intracardiac electrograms or from surface ECG recordings.

The selection of one or more ventricular chambers then includes selecting one or more ventricular chambers in which to provide pacing pulses based on the duration interval of the QRS complex and the delay between the left ventricular and the right ventricular sensed intrinsic ventricular depolarizations. For example, in selecting one or more ventricular chambers, a suggestion to pace in a left ventricle is made when the duration interval of the one or more QRS complexes is greater than or equal to a first threshold value and the difference between the left ventricular and the right ventricular sensed intrinsic ventricular depolarizations is greater than a second threshold value. In one embodiment, the first threshold value is 120 millisecond and the second threshold value is zero (0). Alternatively, in selecting one or more ventricular chambers, a suggestion to pace in both the left ventricle and the right ventricle is made when the duration interval of one or more QRS complexes is greater than or equal to the first threshold value and the difference between the left ventricular and the right ventricular sensed intrinsic ventricular depolarizations is greater than the second threshold value. Finally, in selecting one or more ventricular chambers, a suggestion to pace in a right ventricle when the duration interval of one or more QRS complexes is greater than or equal to the first threshold value and the difference between the left ventricular and the right ventricular sensed intrinsic ventricular depolarizations is less than or equal to the second threshold value. In one embodiment, this suggestion is made through the use of either an implantable pulse generator and/or a medical device programmer.

In one embodiment, the apparatus of the present subject matter includes at least one receiver, where the receiver receives intrinsic intracardia electrograms from the left ventricle and the right ventricle. These electrograms include a left ventricular and a right ventricular sensed intrinsic ventricular depolarizations having QRS complexes. In an additional embodiment, the receiver receives the QRS duration interval of one or more QRS complexes measured from a surface ECG.

The apparatus further includes a controller, where the controller determines a timing relationship between intrinsic electrograms recorded from the left and right ventricle. In one embodiment, the controller calculates a delay between the left ventricular and the right ventricular sensed intrinsic ventricular depolarizations and is adapted to receive a duration interval of one or more QRS complexes. In one embodiment, the QRS duration interval is provided to the controller from measurements made from a surface ECG recording. In an alternative embodiment, the controller determines the duration interval of the QRS complexes from the sensed cardiac signals.

The apparatus further includes a ventricular chamber selector. The ventricular chamber selector selects one or more ventricular chambers in which to provide pacing pulses based on the timing relationship between intrinsic intracardia electrograms recorded from the right and left ventricle. In one embodiment, the ventricular chamber selector selects one or more ventricular chambers in which to provide pacing pulses based on the duration interval of the QRS complexes and the delay between the left ventricular and the right ventricular sensed intrinsic ventricular depolarizations, as described above. The apparatus of the present subject matter can be incorporated into a medical device programmer and/or an implantable pulse generator, where the implantable pulse generator includes a first cardiac lead and a second cardiac lead, where the first and second cardiac leads each include electrodes for sensing the intrinsic intracardia electrograms from the left ventricle and the right ventricle.

DETAILED DESCRIPTION

Figure 1:
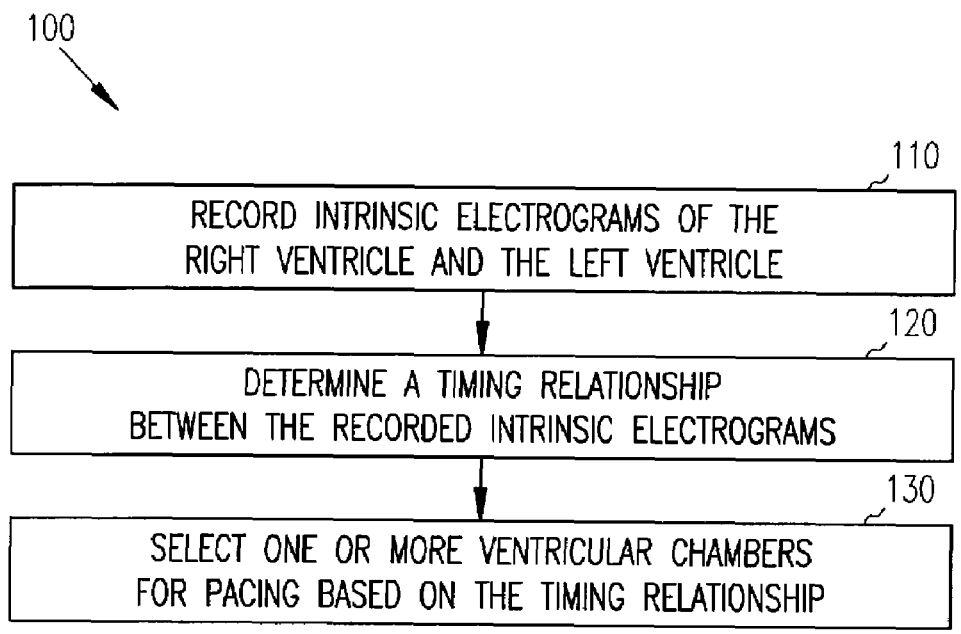
FIG. 1 is one embodiment of a method according to the present subject matter.

In the following detailed description, reference is made to the accompanying drawings that form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents.

The present methods and apparatus will be described in applications involving implantable medical devices for treating heart failure including, but not limited to, implantable pulse generators such as pacemakers, cardioverter/defibrillators, pacer/defibrillators, and biventricular or other multi-site resynchronization devices. However, it is understood that the present methods and apparatus may be employed in unimplanted devices, including, but not limited to, external pacemakers, cardioverter/defibrillators, pacer/defibrillators, biventricular or other multi-site resynchronization devices, monitors, medical device programmers and recorders.

In one embodiment, the present subject matter is implemented in an implantable pulse generator. The implantable pulse generator includes cardiac leads that allow for ventricular cardiac signals to be sensed from left and right ventricular regions of the heart. From information derived from the sensed cardiac signals a selection is made as to which of either the right, left or both ventricular chambers of the heart is to be paced. In one example, relative delays between intrinsic cardiac depolarizations of the right and left ventricles are used to determine which, or both, ventricular chamber is to be paced.

In one embodiment, the ventricle that is activated later (as measured by a later intracardiac lead depolarization) is selected as the stimulation chamber. Since only detection of intracardiac depolarizations are needed, the present subject matter is useful as an automatic site-optimization feature in a ventricular resynchronization therapy device, such as a biventricular stimulation device.

In one embodiment, the suggestion for which ventricular chamber to stimulate (left, right or both) is based on the sensed cardiac conduction between the right and left ventricles of the heart. Different timing relationships between cardiac complexes in the cardiac signals sensed from the right and left ventricular regions can indicate different conduction disorder types. For example, in branch bundle block type disorders regions of the left or right ventricle do not contract together in a coordinated fashion. As a result, the left and right ventricles do not contract simultaneously, but rather, the left ventricle contracts after the right ventricle or vice versa. As a result, the pumping efficiency of the heart is reduced. To increase the pumping efficiency of the heart, identifying and selecting a ventricular pacing location, or locations, that allow for synchronized ventricular contractions would be beneficial to patients with conduction disorder problems. The present subject matter addresses these issues.

FIG. 1 shows one embodiment of a method 100 according to the present subject matter. At 110, intrinsic electrograms of the right ventricle and the left ventricle are recorded. In one embodiment, the electrogram recordings are made from both a right ventricular location and a left ventricular location through the use of electrodes implanted within and/or on the surface of the heart. For example, the electrograms are sensed as unipolar cardiac signals using an implantable pulse generator coupled to one or more cardiac leads implanted in or adjacent the right ventricle and/or left ventricle. In addition, bipolar cardiac signals are sensed from the left and right ventricles so as to allow for ventricular depolarizations to be sensed from around the distal portions of the implanted leads.

At 120, a timing relationship is determined between intrinsic electrograms of the left and right ventricle. In one embodiment, the electrograms include indications of ventricular depolarizations, such as R-waves and/or QRS-complexes that are both indicators of intrinsic ventricular depolarizations. In one embodiment, the timing relationship includes calculating a delay between the left ventricular and the right ventricular sensed intrinsic ventricular depolarizations. For example, the delay between left ventricular and the right ventricular sensed intrinsic ventricular depolarizations is taken as the difference between a time of a first ventricular contraction in a first ventricular chamber (e.g., left ventricle or right ventricle) and a time of a second ventricular contraction in a second ventricular chamber (e.g., the right ventricle when the first chamber is the left ventricle and the left ventricle when the first chamber is the right ventricle), where the two ventricular contractions are part of the same cardiac contraction and both contribute to one cardiac cycle of the heart.

Determining the timing relationship also includes measuring a duration interval of one or more QRS complexes. Measuring the duration interval of QRS complexes is accomplished in any number of ways. For example, the duration interval of the QRS complexes is measured manually from a printout of a surface ECG measurement. Alternatively, the duration interval of the QRS complexes is measured electronically from the sensed and recorded cardiac electrograms.

At 130, one or more ventricular chambers in which to provide pacing pulses are then selected based on the timing relationship between intrinsic electrograms of the right and the left ventricles. In one embodiment, the selection at 130 is based on the duration interval of the QRS complex and a calculated delay between the left ventricular and the right ventricular sensed intrinsic ventricular depolarizations.

Figure 2:
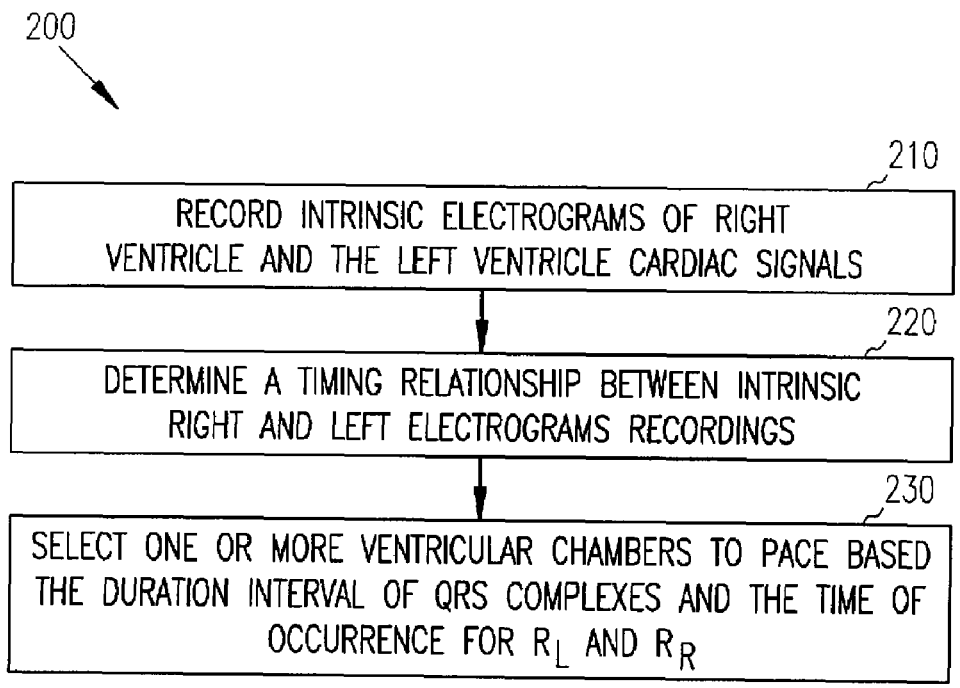
FIG. 2 is one embodiment of a method according to the present subject matter.

FIG. 2 shows an additional embodiment of a method 200 according to the present subject matter. At 210, intrinsic intracardia electrograms of right ventricular and left ventricular cardiac signals are recorded. In one embodiment, the right and left ventricular cardiac signals are sensed as unipolar cardiac signals using an implantable pulse generator coupled to one or more cardiac leads implanted in or adjacent the right ventricle and/or left ventricle. In one embodiment, a first cardiac signal is sensed from a right ventricular region and a second cardiac signal is sensed from a left ventricular region. In one embodiment, the first cardiac signal is sensed from an apex of the right ventricle, while the second cardiac signal is sensed from a left ventricular free wall. Alternatively, the second cardiac signal is sensed from electrodes implanted transvenously through the coronary sinus so as to position the electrodes adjacent the left ventricle. In an additional embodiment, the electrograms are sensed through the use of a surface 12-lead ECG measurement or a PRM surface ECG system.

At 220, the timing relationship is determined between intrinsic right and left electrograms recordings. In one embodiment, a portion of the timing relationship is determined by calculating a delay between a first ventricular chamber (e.g., left ventricle or right ventricle) and a time of a second ventricular contraction in a second ventricular chamber (e.g., the right ventricle when the first chamber is the left ventricle and the left ventricle when the first chamber is the right ventricle), where the two ventricular contractions are part of the same cardiac contraction and both contribute to one cardiac cycle of the heart. For example, cardiac depolarizations are detected in each of the right and left cardiac signals. In one embodiment, the cardiac depolarizations include R-waves, which are indications of ventricular contractions. The time at which the ventricular contractions occurred is then recorded, where $R_L$ is designated as the time at which the depolarization in the left ventricle occurred and $R_R$ is designated as the time at which the depolarization in the right ventricle occurred. In one embodiment, the time the R-wave occurred is taken as the peak (i.e., the point of maximum deflection during depolarization) of the sensed intrinsic ventricular depolarizations (e.g., the R-waves). The delay between the ventricular chambers is then calculated by taking the difference between the detected peaks of the intrinsic ventricular depolarizations sensed from the left ventricle and the right ventricle (i.e., the difference between $R_L$ and $R_R$). The difference between $R_L$ and $R_R$ is then used in determining which, or both, ventricular chamber should be paced.

The timing relationship also includes measuring a duration interval of one or more QRS complexes. Measuring the duration interval of QRS complexes is accomplished in any number of ways. For example, the QRS complex duration interval is manually measured. Measuring the QRS complex duration interval is accomplished by sensing the electrograms using any of the above-mentioned techniques and recording/printing the sensed cardiac signal on a paper strip chart recording at 50 millimeters/second. In one embodiment, the QRS complex duration intervals are measured from cardiac signals sensed on leads II, $V_1$ and $V_6$ of a 12-lead ECG, where lead $V_6$ is placed at the midaxillary line, at the same level as lead $V_4$. Alternatively, QRS complex duration intervals are measured from cardiac signals sensed from leads II and $V_1$ of a PRM surface ECG system, where lead $V_1$ is placed at the fourth intercostal space, just to the right of the sternum. In one embodiment, the QRS duration is measured from the printout of the cardiac signal using standard practice for determining the start and end of the QRS complex. For example, the QRS duration is measured between a point at which the initial deflection for the Q-wave is sensed and a point where the S-wave returns to baseline of the cardiac signal. Alternatively, the QRS duration is measured from individual leads, where the maximum duration of the QRS interval from among the individual leads is taken as the final result.

At 230, one or more ventricular chambers are selected in which to provide pacing pulses based on the timing relationship between intrinsic electrograms recorded of the right and the left ventricles. In one embodiment, this selection is based on the duration interval of the QRS complexes and the time of occurrence for $R_L$ and $R_R$. For example, the determination as to the ventricular chamber or chambers to pace is based on the comparison of the duration interval of the QRS complexes to an established value and the value of the difference between $R_L$ and $R_R$. So, when the duration interval of the QRS complexes is greater than or equal to a first threshold value and the difference between $R_L$ and $R_R$ (i.e., $R_L-R_R$) is greater than a second threshold value, then the patient is likely a left bundle branch block type. In this situation the suggested pacing chamber would be either the left ventricle or biventricular (left ventricle and right ventricle). Alternatively, when the duration interval of the QRS complexes is greater than or equal to the first threshold value and the difference between $R_L$ and $R_R$ (i.e., $R_L-R_R$) is less than or equal to the second threshold value, then the patient is likely a right bundle branch block type. In this situation the suggested pacing chamber would be the right ventricle. In one embodiment, the first threshold value is set at 120 milliseconds and the second threshold value is set at zero (0).

Figure 3A:
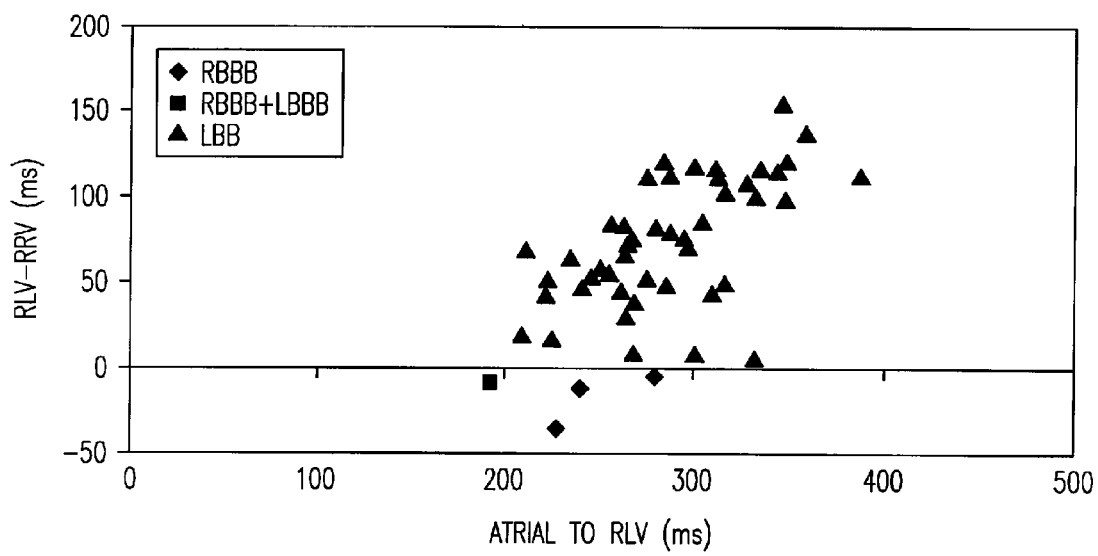
FIG. 3A shows patient data on a scatter plot of $R_{LV}$-$R_{RV}$ intervals (ms) vs. Atrial to $R_{LV}$ intervals (ms)
Figure 3B:
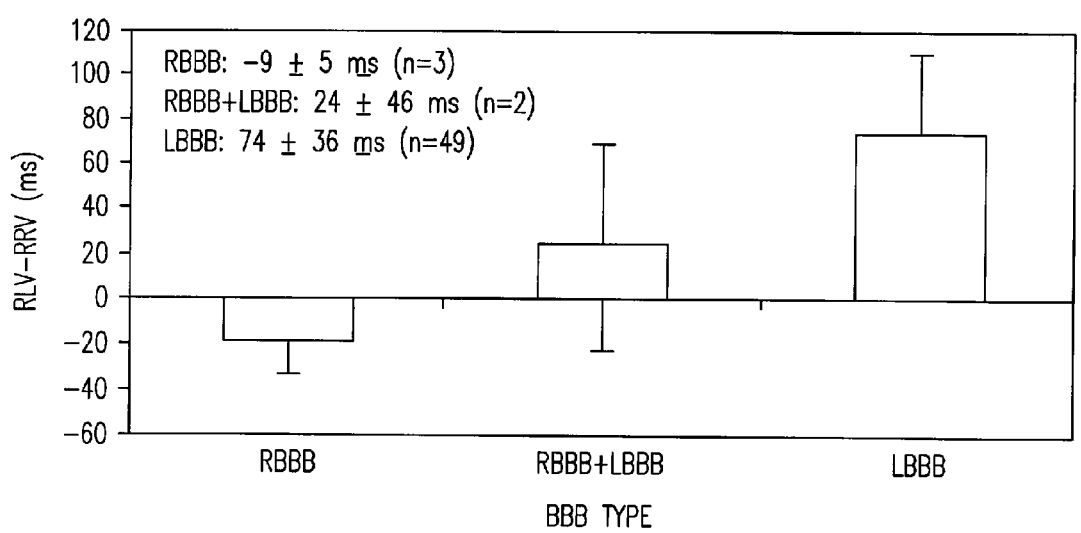
FIG. 3B shows patient data on a bar graph of $R_{LV}$-$R_{RV}$ intervals (ms) vs. Bundle Branch Block Type.

FIGS. 3A and 3B show data collected from fifty four (54) human patients receiving ventricular resynchronization therapy. The data indicate that when QRS complexes have a duration interval greater than or equal to 120 milliseconds, the decision as to whether a patient has a left bundle branch block or a right bundle branch block can be determined by the value of the difference between the $R_L$ and $R_R$ values, as previously described.

As mentioned previously, the present subject matter is implemented in any number of implantable or external medical devices. These medical devices include, but are not limited to, implantable pulse generators, such as pacemakers and cardioverter/defibrillators, pacer/defibrillators, and biventricular or other multi-site resynchronization devices. Other devices include, but are not limited to, external pacemakers, cardioverter/defibrillators, pacer/defibrillators, biventricular or other multi-site resynchronization devices, monitors, medical device programmers and recorders.

Figure 4:
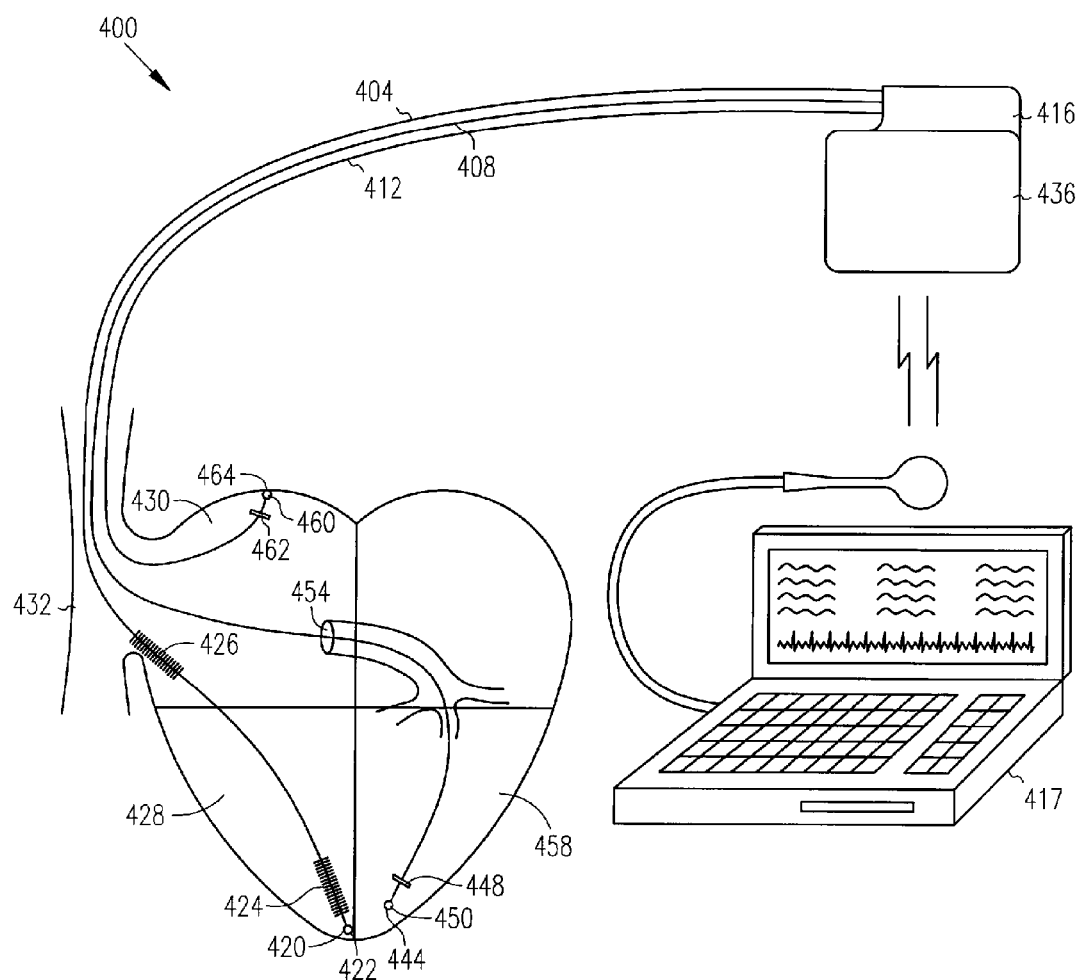
FIG. 4 is a schematic view of a medical device programmer and an implantable medical device with leads implanted in a heart, where portions of the heart have been removed to show detail, according to one embodiment of the present subject matter.

FIG. 4 shows one embodiment of an implantable pulse generator system 400 according to the present subject matter. The implantable pulse generator system 400 includes biventricular pacing ability, the ability to sense cardiac signals from and provide pacing pulses to both the right and left ventricular regions of the heart.

Examples of biventricular pacemakers include U.S. Pat. Nos. 5,792,203 and 4,928,688, which are hereby incorporated by reference in their entirety.

Biventricular pulse generators have been found to be useful in treating heart failure (HF), a clinical syndrome in which an abnormality of cardiac function causes cardiac output to fall below a level adequate to meet the metabolic demand of peripheral tissues. HF can be due to a variety of etiologies, with ischemic heart disease being the most common. Some HF patients suffer from some degree of AV block such that their cardiac output can be improved by synchronizing atrial and ventricular contractions with dual-chamber pacing using a short programmed AV delay time. It has also been shown, however, that some HF patients suffer from intraventricular conduction defects (a.k.a. bundle branch blocks). The cardiac outputs of these can be increased by improving the synchronization of right and/or left ventricular contractions. Identifying which, or both, ventricular chamber to pace is then important in treating these cardiac conditions.

In FIG. 4, the implantable pulse generator 400 includes a first cardiac lead 404, a second cardiac lead 408 and a third cardiac lead 412. Each lead 404, 408 and 412 further includes an insulative lead body that includes insulated lead conductors that couple connector pins and/or rings at a proximal end of lead to each electrode on the lead 404, 408 and 412. The implantable pulse generator 400 further includes a connector block 416 adapted to releasable couple leads 404, 408 and 412 to the pulse generator and to couple the electrodes located on the leads to the electronic control circuitry located within the implantable pulse generator 400. The electronic circuitry within the implantable pulse generator 400 senses cardiac signals from the heart and provides electrical pulses, such as pacing and/or defibrillation pulses, under predetermined conditions of the heart. The electronic circuitry also contains transmitting and receiving circuitry for communicating with an external medical device programmer 417.

In the embodiment shown in FIG. 4, the first cardiac lead 404 includes a first ventricular pacing/sensing electrode 420 positioned at or near a distal end 422 of the first cardiac lead 404. The first cardiac lead 404 further includes a first defibrillation electrode 424 and a second defibrillation electrode 426, where the electrodes 424 and 426 are positioned on lead 404 to allow the first pacing/sensing ventricular electrode 420 and the first defibrillation electrode 424 to be positioned in a right ventricle 428 and the second defibrillation electrode 426 positioned in at least a portion of a right atrium 430 and/or a portion of a major vein to the heart, such as the superior vena cava 432.

Electrodes 424 and 426 allow for bipolar cardiac signals to be sensed from the right ventricular region, while electrode 420 allows for unipolar (near-field) cardiac signals to be sensed from the right ventricle. In addition, electrodes 420, 424 and 426 and the implantable pulse generator housing 436, in a "hot can" configuration, allow for different combinations of electrodes and the housing 436 to be used in sensing the cardiac signals from and for delivering electrical energy pulses to at least the right ventricular region of the heart.

The second cardiac lead 408 includes a second ventricular sensing/pacing electrode 444 and a third ventricular sensing/pacing electrode 448. In one embodiment, the second ventricular sensing/pacing electrode 444 is a full or partial annular ring electrode positioned at or near a distal end 450 of the second cardiac lead 408. Alternatively, the second ventricular sensing/pacing electrode 444 is a distal tip electrode positioned at the distal end of the second cardiac lead 408. The third ventricular sensing/pacing electrode 448 is positioned on the lead 408 proximal to the second electrode 444 to allow for the electrodes 444 and 448 to be positioned within a coronary vein 454 and through the coronary veins (such as the lateral or posterior vein) so that the electrodes 444 and 448 are adjacent the left ventricle 458 to allow for sensing intrinsic heart signals from the left ventricle 458 and providing one or more of resynchronization stimulations or defibrillation shocks. In one embodiment, the second cardiac lead 408 of a size and shape adapted to be positioned through the coronary sinus vein 454 so as to allow the electrodes 444 and 448 to be positioned adjacent the left ventricle 458.

Electrodes 444 and 448 allow for bipolar cardiac signals to be sensed from and pacing pulses to be delivered to the left ventricular region of the heart. Alternatively, unipolar cardiac signals could be sensed and coordinated paces shocks could be delivered between either electrode 444 or 448 and the housing 436 of the implantable pulse generator.

The third cardiac lead 412 includes a first atrial sensing/pacing electrode 460 and a second atrial sensing/pacing electrode 462, where both electrodes 460 and 462 are spaced apart and positioned at or near a distal end 464 of the third cardiac lead 412. In one embodiment, the first atrial sensing/pacing electrode 460 is used in conjunction with the housing 436 for unipolar pacing or sensing from the right atrium 430. Alternatively, the first and second electrodes 460 and 462 are used to pace bipolarly or to sense bipolar cardiac signals between the two electrodes 460 and 462. Additional pacing/sensing electrodes can be included on the third cardiac lead 412 to allow for bipolar sensing and pacing of the right atrium 430.

The apparatus of the present subject matter is not limited to an implantable pulse generator. The apparatus of the present subject matter can be generally considered to be implemented as an automatic site-optimization feature in ventricular resynchronization therapy that can be carried out by an external apparatus (e.g., a medical device programmer or external ventricular resynchronization therapy device) or an implantable pulse generator (e.g., an implantable ventricular resynchronization therapy device such as a pacemaker and/or a cardioverter/defibrillator).

Figure 5:
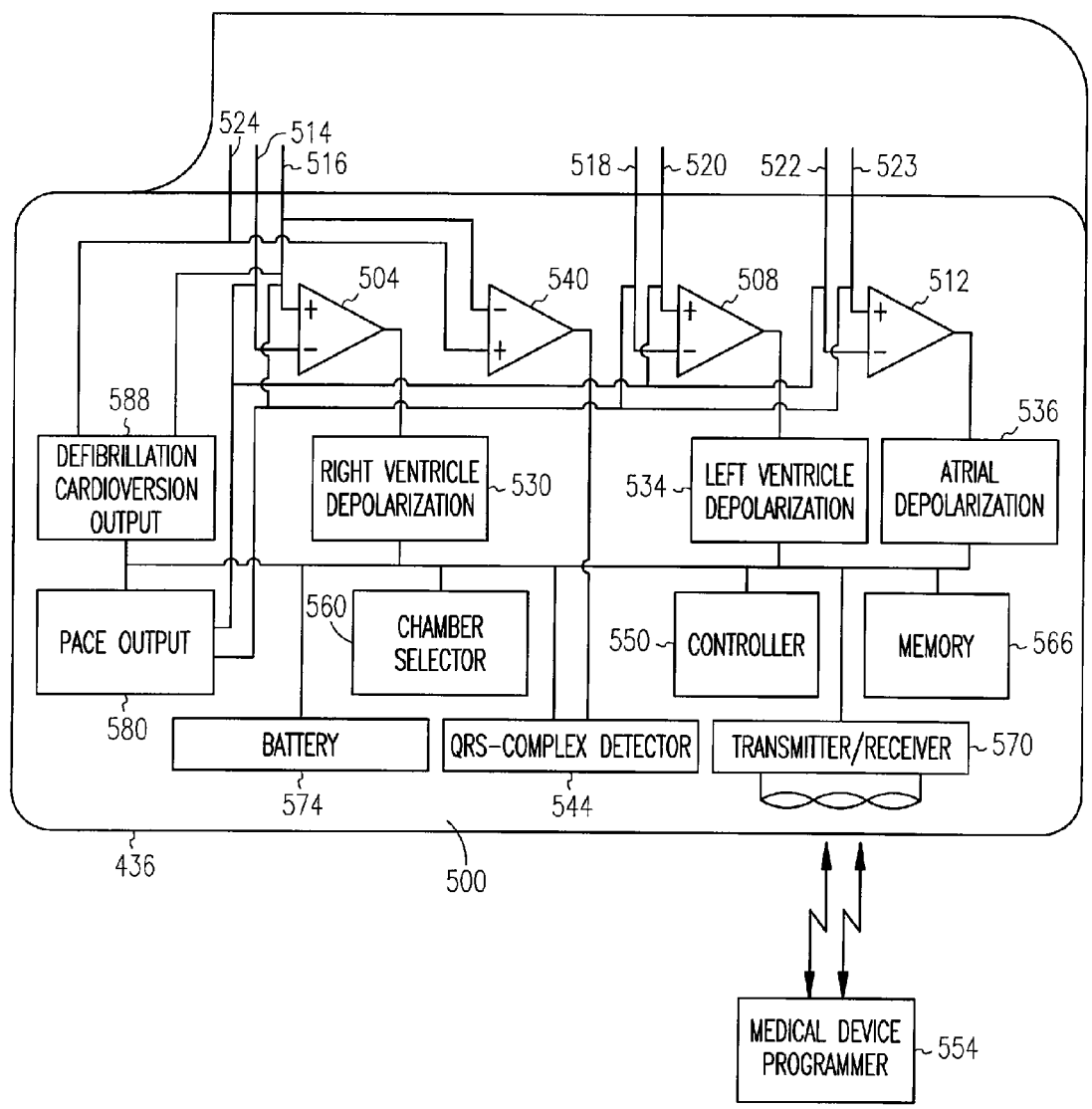
FIG. 5 is a block diagram of an implantable medical device according to one embodiment of the present subject matter.

FIG. 5 is a schematic drawing illustrating generally by way of example, but not by way of limitation, one embodiment of the implantable pulse generator 400 coupled by leads 404, 408 and 412 to the heart. In one such embodiment, the implantable pulse generator 400 provides biventricular resynchronization therapy to coordinate right ventricular and left ventricular contractions, such as for heart failure patients. FIG. 5 shows one embodiment of control circuitry 500 within the implantable pulse generator housing 436. The housing 436 is electrically conductive and acts as a reference electrode in unipolar pacing and sensing.

In the present embodiment, the implantable pulse generator 400 is adapted to receive the first, second and third leads 404, 408 and 412, in connector block 416 and to couple electrodes 420, 424, 444, 448, 460 and 462 on the cardiac leads to at least one receiver, where the receiver receives intrinsic intracardia electrograms from a left ventricle and a right ventricle. In the present embodiment, the at least one receiver includes cardiac signal amplifiers 504, 508 and 512 that receive cardiac signals from electrodes 420, 424, 444, 448, 460 and 462 via contacts 514, 516, 518, 520, 522 and 523, respectively. Contact 524 is provided to couple to electrode 426.

In one embodiment, any combination of bipolar and/or unipolar cardiac signals are sensed using the electrodes 420, 424, 444, 448, 460 and 462. For example, a unipolar cardiac signal is sensed from the right ventricle between electrode 422 and the housing 436. In addition, a unipolar cardiac signal is sensed from the left ventricle between electrode 444 or 448 and the housing 436. In one embodiment, QRS complex duration intervals are sensed and measured, as described above, from the unipolar cardiac signal sensed from the right ventricle and/or the left ventricle. Finally, a unipolar cardiac signal from the right atrium is sensed from either the first or second atrial sensing/pacing electrode (460 or 462) and the housing 436.

In one embodiment, an output from amplifier 504 is shown coupled to a right ventricular depolarization sensor 530 to allow for a bipolar cardiac signal to be sensed from the right ventricle 428 (FIG. 4) between the first ventricular pacing/sensing electrode 420 and the first defibrillation electrode 424. The output from amplifier 508 is shown coupled to a left ventricular depolarization sensor 534 to allow for a bipolar cardiac signal to be sensed from the left ventricle 458 (FIG. 4) between the second ventricular sensing/pacing electrode 444 and the third ventricular sensing/pacing electrode 448. The output from amplifier 512 is shown coupled to an atrial depolarization sensor 536 to allow for a bipolar cardiac signal to be sensed between the first and second atrial sensing/pacing electrodes 460 and 462.

The control circuitry 500 further includes amplifier 540 that is coupled to the first defibrillation electrode 424 and the second defibrillation electrode 426 to allow for bipolar far-field cardiac signals to be sensed from the heart. From this signal it is possible to measure the duration interval of sensed QRS complexes and to use this value as previously described. In an additional embodiment, the housing 436 is used as an additional electrode in common with the second defibrillation electrode 426 to allow for the far-field cardiac signal to be sensed between the first defibrillation electrode 424 and the second defibrillation electrode 426/housing 436. The output from amplifier 540 is shown coupled to a QRS-complex detector 540. In one embodiment, the QRS-complex detector 540 identifies QRS-complexes detected in the cardiac signal from amplifier 540 and supplies this information to controller 550 either for further processing by the controller 550 or for being transmitted to a medical device programmer 554, as will be described below.

The information from the right ventricular depolarization sensor 530 and the left ventricular depolarization sensor 534 are then used by the controller 550 to determine the timing relationship between the intrinsic intracardia electrograms recorded from the left and right ventricle. In one embodiment, the controller 550 calculates a delay between the left ventricular and the right ventricular sensed intrinsic ventricular depolarizations. In one example, the controller 550 detects peaks of the sensed intrinsic ventricular depolarizations and calculates the delay between the detected peaks of the intrinsic ventricular depolarizations sensed from the left ventricular and the right ventricles.

In addition to calculating the delay, the controller 550 also receives a duration interval of one or more QRS complexes. In one embodiment, the duration interval of the QRS complexes is calculated by the QRS-complex detector 544. Alternatively, the duration interval is calculated from the paper strip chart recording of the ventricular signals, as previously described, and supplied to the controller 550 from the medical device programmer 554.

The control circuitry 500 further includes a ventricular chamber selector 560 coupled to the controller 550. The ventricular chamber selector 560 selects one or more ventricular chambers in which to provide pacing pulses based on the timing relationship between intrinsic intracardia electrograms recorded from the right and left ventricle. In one embodiment, the ventricular chamber selector 560 selects one or more ventricular chambers in which to provide pacing pulses based on the duration interval of the QRS complexes and the delay between the left ventricular and the right ventricular sensed intrinsic ventricular depolarizations, as previously discussed. For example, the ventricular chamber selector 560 identifies a left ventricle for pacing when the duration interval of the one or more QRS complexes is greater than or equal to 120 milliseconds and the difference between the left ventricular and the right ventricular sensed intrinsic ventricular depolarizations is greater than zero (0). Additionally, the ventricular chamber selector 560 identifies both a left ventricle and a right ventricle for pacing when the duration interval of the one or more QRS complexes is greater than or equal to 120 milliseconds and the difference between the left ventricular and the right ventricular sensed intrinsic ventricular depolarizations is greater than zero (0). Finally, the ventricular chamber selector 560 identifies a right ventricle for pacing when the duration interval of one or more QRS complexes is greater than or equal to 120 milliseconds and the difference between the left ventricular and the right ventricular sensed intrinsic ventricular depolarizations is less than or equal to zero (0).

The controller 550 also analyzes the sensed cardiac signals to determine when and if to deliver electrical energy pulses to the heart. In one embodiment, the microprocessor implements one or more analysis protocols stored in a memory 566 to analyze one or more of the sensed cardiac signals and to provide pacing, cardioversion and/or defibrillation therapy to one or more chambers of the heart under certain predetermined conditions. Memory 566 is also used to store one or more sensed cardiac signals to be downloaded to the medical device programmer 554 for analysis. In one embodiment, the control circuitry 500 communicates with the medical device programmer 554 through a receiver/transmitter 570, where cardiac signals, programs and operating parameters for the programs for the implantable medical device are transmitted and received through the use of the programmer 556 and the transmitter/receiver 570. Power for the control circuitry 500 is supplied by a battery 574.

The controller 550 further controls a pace output circuit 580 and a defibrillation output circuit 588 to provide pacing, cardioversion and/or defibrillation therapy to one or more chambers of the heart under certain predetermined conditions. In one embodiment, the pace output circuit 580 is coupled to contacts 514, 516, 518, 520, 522 and the housing 436 to allow for pacing between the electrode combinations of 420 and 424, 420 and the housing 436, 444 and 448, 444 or 448 and the housing 436, 460 and 462, and 460 and the housing 436. The defibrillation output circuit 588 is shown coupled to electrodes 424, 426 and (optionally) housing 436 to allow for defibrillation energy pulses to be delivered to a heart.

Figure 6:
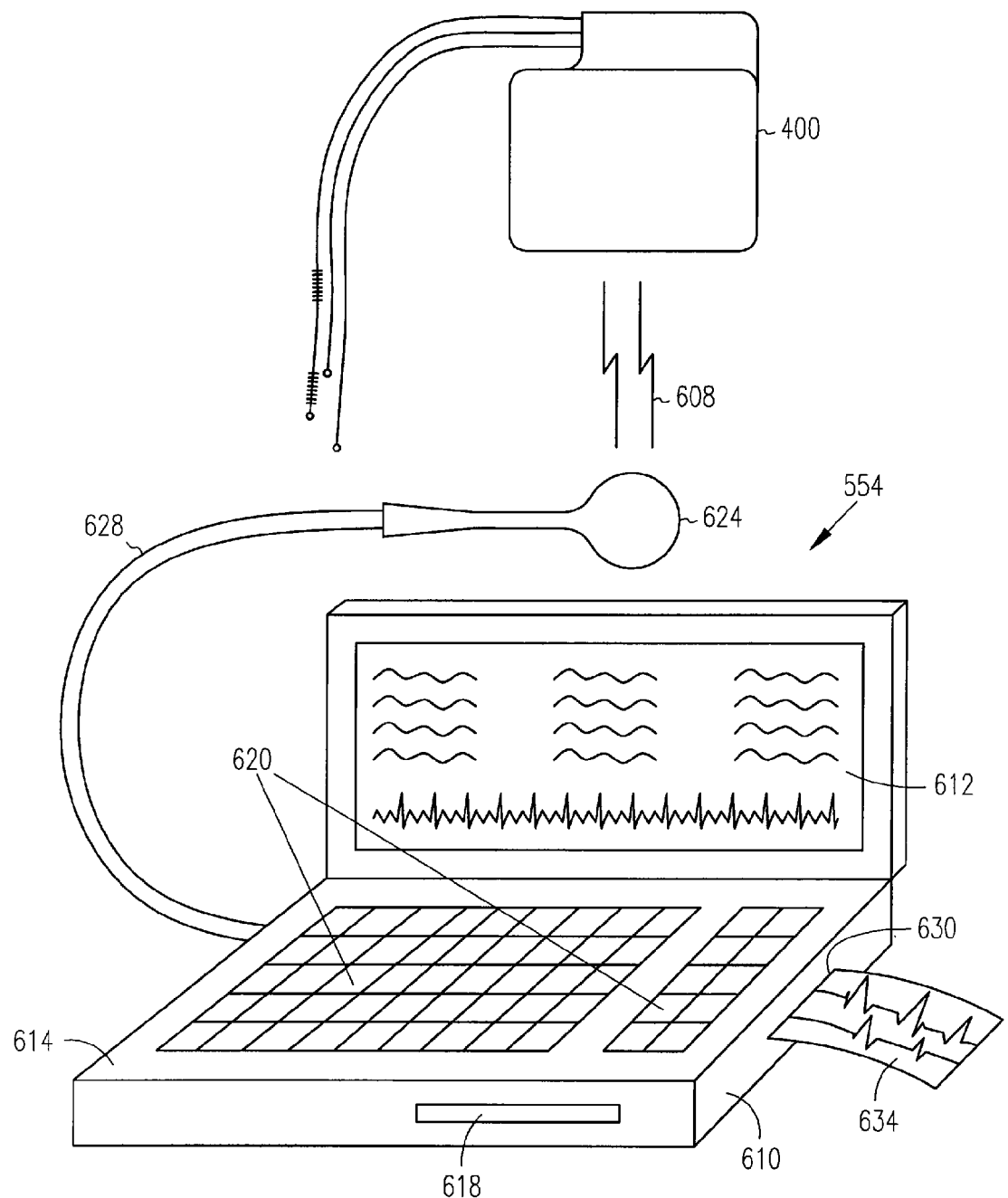
FIG. 6 is a perspective view of a medical device programmer and an implantable medical device with leads according to one embodiment of the present subject matter.

FIG. 6 shows one embodiment of a medical device programmer 554 according to the present subject matter. The medical device programmer 554 is adapted to be positioned outside the human body for communication with the implantable pulse generator 400, as previously described. In one embodiment, a communication link 608 is established between the medical device programmer 554 and the implantable pulse generator 400, as described above.

In one embodiment, the medical device programmer 554 includes electronic circuitry within a housing 610, where a graphics display screen 612 is disposed on an upper surface 614 of the housing 610. The programmer 554 further includes a drive 618 for reading and writing instructions used by the electronic circuitry of the programmer 554. The graphics display screen 612 is operatively coupled to the electronic circuitry within the housing 610 and is adapted to provide a visual display of graphics and/or data to the user.

The programmer 554 further includes input devices to the electronic circuitry. For example, the programmer 554 includes a touch-sensitive display screen, such that the user interacts with the electronic circuitry by touching identified regions of the screen with either their finger or with a stylus (not shown). In addition, the programmer 554 further includes an alphanumeric key board 620 for providing information, such as programmable values for the implantable medical device 604, to the electronic circuitry and the medical device 604.

The programmer 554 further includes a programming head 624. The programming head 624 is used to establish the communication link 608 between the electronic circuitry within the programmer 554 and the implantable pulse generator 400. In one embodiment, the communication link 608 is a radio frequency link. The telemetry link between the implantable pulse generator 400 and the programmer 554 allows the electronic circuitry coupled to the graphics display screen 612 to be coupled to the electronic control circuitry of the implantable pulse generator 400. The programming head 624 is coupled to the electronic circuitry of the medical device programmer through cable 628. FIG. 6 also shows the programmer 554 having a printer 630 which allows for cardiac signals received from the implantable pulse generator 400 and displayed on the graphics display screen 612 to be displayed on a paper printout 634. Adjustments for printer speed and scale of the printed cardiac signals is adjustable through the use of the display screen 612 and the electronic circuitry within the programmer 600.

Figure 7:
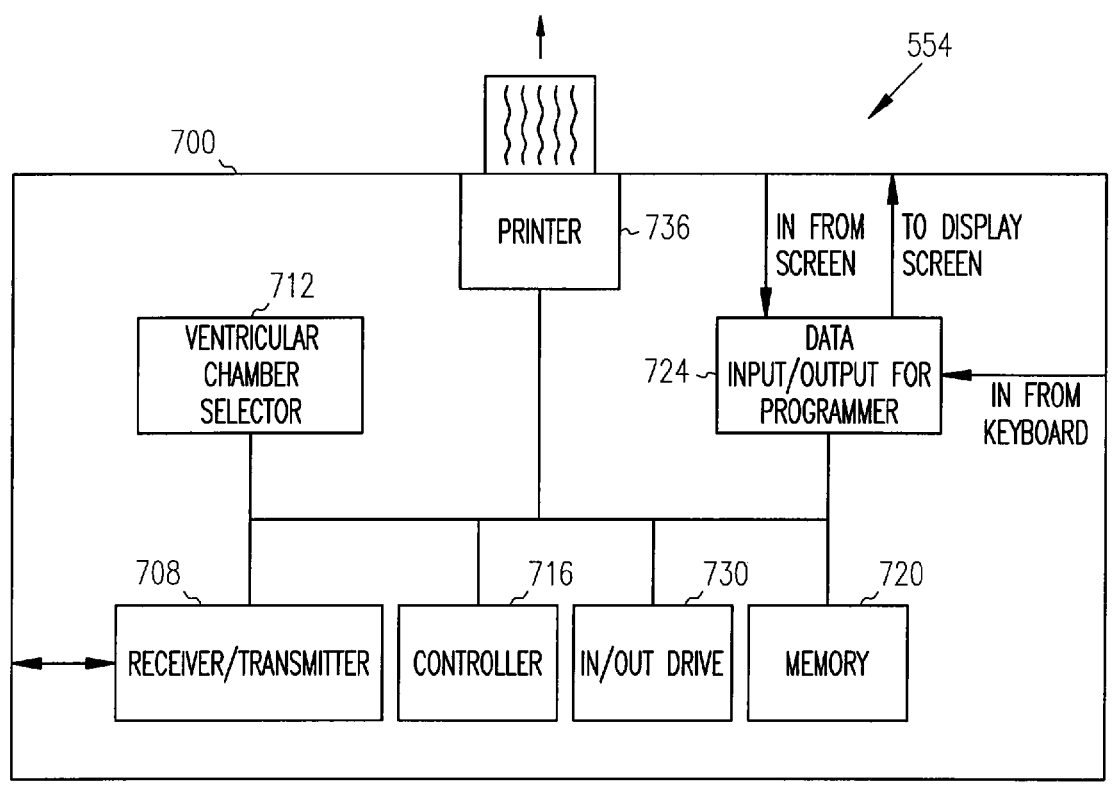
FIG. 7 is a block diagram of a medical device programmer according to one embodiment of the present subject matter.

FIG. 7 shows one embodiment of control circuitry 700 for the programmer 554. The control circuitry 700 includes a receiver/transmitter circuit 708, a ventricular chamber selector 712, a controller 716, a memory 720, a data input/output 724 and an in/out drive 730. In one embodiment, the receiver/transmitter circuit 708 receives intrinsic intracardia electrograms from a left ventricle and a right ventricle. In one embodiment, the intrinsic intracardia electrograms from the left ventricle and the right ventricle are sensed using an implantable pulse generator, as previously described. The controller 716 then determines a timing relationship between intrinsic intracardia electrograms recorded from the left and right ventricle. In one embodiment, the controller 716 calculates the delay between the left ventricular and the right ventricular sensed intrinsic ventricular depolarizations. In one embodiment, the controller 716 detects peaks of the sensed intrinsic ventricular depolarizations and calculates the delay between the detected peaks of the intrinsic ventricular depolarizations sensed from the left ventricular and the right ventricles, as previously described.

The controller is also adapted to receive the duration interval of one or more QRS complexes. In one embodiment, the duration interval of the QRS complexes are measured from a print-out of the sensed electrograms, as previously described, where the electrograms are printed on printer 736 under the control of controller 716 and under the directions provided through the data input/output 724. The QRS duration interval is then provided through the data input/output 724 via prompts displayed on the display screen 612 (not shown in FIG. 7) and data received via the keyboard 620 (not shown in FIG. 7). In an additional embodiment, the QRS duration is measured from printout from a surface ECG and then manually entered into the control circuitry 700.

The ventricular chamber selector 712 then selects one or more ventricular chambers in which to provide pacing pulses based on the timing relationship between intrinsic intracardia electrograms recorded from the right and left ventricle. In one embodiment, the timing relationship used is based on the duration interval of the QRS complexes and the delay between the left ventricular and the right ventricular sensed intrinsic ventricular depolarizations, as previously described. The results are then displayed on the display screen 612. The user can then elect to accept the suggested results and program the implantable medical device with the suggested settings.

Although specific embodiments have been illustrated and described herein, it will be appreciated by those of ordinary skill in the art that any arrangement which is calculated to achieve the same purpose may be substituted for the specific embodiment shown. This application is intended to cover any adaptations or variations of the present invention. Therefore, it is intended that this invention be limited only by the claims and the equivalents thereof.

We claim:

1. A medical device programmer, comprising:
   a receiver/transmitter circuit for communicating with an implantable cardiac device;
   circuitry for receiving data from the implantable cardiac device that includes a timing relationship between intrinsic ventricular depolarizations of the left and the right ventricle and further includes a duration of a QRS complex; and,
   circuitry for selecting one or more ventricular chambers in which to provide pacing pulses based on the timing relationship between intrinsic ventricular depolarizations of the left and the right ventricle and the duration of a QRS complex.

2. The programmer of claim 1 further comprising circuitry for determining a duration of a QRS complex from a cardiac signal.

3. The programmer of claim 2 wherein the cardiac signal from which the QRS duration is determined is received from the implantable cardiac device.

4. The programmer of claim 2 wherein the cardiac signal from which the QRS duration is determined is a surface ECG.

5. The programmer of claim 1 further comprising:
   data input/output circuitry; and,
   wherein the duration of the QRS complex is input via the data input/output circuitry.

6. The programmer of claim 1 wherein the data from the implantable cardiac device that indicates a timing relationship between intrinsic ventricular depolarizations of the left and the right ventricle are intra-cardiac electrograms.

7. The programmer of claim 1 wherein the data from the implantable cardiac device that indicates a timing relationship between intrinsic ventricular depolarizations of the left and the right ventricle includes an interval between a right ventricular sense $R_R$ and a left ventricular sense $L_L$.

8. The programmer of claim 1 further comprising:
   data input/output circuitry interfaced to a display screen; and,
   wherein the circuitry for selecting one or more ventricular chambers in which to provide pacing pulses displays the selection on the display screen.

9. The programmer of claim 1 wherein the circuitry for selecting one or more ventricular chambers in which to provide pacing pulses includes circuitry for suggesting pacing in the left ventricle when the duration of the QRS complex is greater than or equal to a first threshold value and the delay between the right ventricular and the left ventricular intrinsic ventricular depolarizations is greater than a second threshold value, with the right ventricular depolarization occurring before the left ventricular depolarization.

10. The programmer of claim 9 wherein the first threshold value is approximately 120 milliseconds and the second threshold value is approximately zero (0).

11. The programmer of claim 1 wherein the circuitry for selecting one or more ventricular chambers in which to provide pacing pulses includes circuitry for suggesting pacing in the right and left ventricles when the duration of the QRS complex is greater than or equal to a first threshold value and the delay between the right ventricular and the left ventricular intrinsic ventricular depolarizations is greater than a second threshold value, with the right ventricular depolarization occurring before the left ventricular depolarization.

12. The programmer of claim 10 wherein the first threshold value is approximately 120 milliseconds and the second threshold value is approximately zero (0).

13. The programmer of claim 1 wherein the circuitry for selecting one or more ventricular chambers in which to provide pacing pulses includes circuitry for suggesting pacing in the right ventricle when the duration of the QRS complex is greater than or equal to a first threshold value and the delay between the left ventricular and the right ventricular intrinsic ventricular depolarizations is greater than a second threshold value, with the left ventricular depolarization occurring before the right ventricular depolarization.

14. The programmer of claim 13 wherein the first threshold value is approximately 120 milliseconds and the second threshold value is approximately zero (0).

15. A method, comprising:
   employing a medical device programmer to receive data from the implantable cardiac device that includes a timing relationship between intrinsic ventricular depolarizations of the left and the right ventricle and further includes a duration of a QRS complex; and,
   selecting one or more ventricular chambers in which to provide pacing pulses based on the timing relationship between intrinsic ventricular depolarizations of the left and the right ventricle and the duration of a QRS complex.

16. The method of claim 15 further comprising determining the duration of a QRS complex from a cardiac signal is received from the implantable cardiac device.

17. The method of claim 15 further comprising determining the duration of a QRS complex from a surface ECG.

18. The method of claim 15 further comprising determining the duration of a QRS complex and inputting the duration to the medical device programmer.

19. The method of claim 15 wherein the data from the implantable cardiac device that indicates a timing relationship between intrinsic ventricular depolarizations of the left and the right ventricle are intra-cardiac electrograms.

20. The method of claim 15 wherein the data from the implantable cardiac device that indicates a timing relationship between intrinsic ventricular depolarizations of the left and the right ventricle includes an interval between a right ventricular sense $R_R$ and a left ventricular sense $L_L$.

* * * * *

UNITED STATES PATENT AND TRADEMARK OFFICE
CERTIFICATE OF CORRECTION

| | | |
|---|---|---|
| PATENT NO. | : 7,546,162 B2 | Page 1 of 1 |
| APPLICATION NO. | : 11/276007 | |
| DATED | : June 9, 2009 | |
| INVENTOR(S) | : Jiang Ding et al. | |

It is certified that error appears in the above-identified patent and that said Letters Patent is hereby corrected as shown below:

On the Title page, in field (57), under "Abstract", in column 2, line 3, delete "intracardia" and insert -- intracardiac --, therefor.

On the Title page, in field (57), under "Abstract", in column 2, line 5, delete "intracardia" and insert -- intracardiac --, therefor.

On the Title page, in field (57), under "Abstract", in column 2, line 15, delete "intracardia" and insert -- intracardiac --, therefor.

In column 13, line 36, in Claim 6, delete "intra-cardiac" and insert -- intracardiac --, therefor.

In column 14, line 50, in Claim 19, delete "intra-cardiac" and insert -- intracardiac --, therefor.

Signed and Sealed this

Thirteenth Day of July, 2010

David J. Kappos
*Director of the United States Patent and Trademark Office*